(12) United States Patent
Gilbert et al.

(10) Patent No.: US 11,944,753 B2
(45) Date of Patent: Apr. 2, 2024

(54) VARIABLE SKIN BREATHABILITY ADHESIVE ARRANGEMENTS FOR PATIENT INTERFACES

(71) Applicant: KONINKLIJKE PHILIPS N.V., Eindhoven (NL)

(72) Inventors: Natasha A Gilbert, Pittsburgh, PA (US); Justin Edward Rothermel, Monroeville, PA (US); Lauren Patricia Chodkowski, Pittsburgh, PA (US); James Maier, Pittsburgh, PA (US); Jonathan Sayer Grashow, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 810 days.

(21) Appl. No.: 17/037,802

(22) Filed: Sep. 30, 2020

(65) Prior Publication Data
US 2021/0093823 A1    Apr. 1, 2021

Related U.S. Application Data (60) Provisional application No. 62/908,027, filed on Sep. 30, 2019.

(51) Int. Cl.
*A61M 16/06*    (2006.01)
(52) U.S. Cl.
CPC ..... *A61M 16/0688* (2014.02); *A61M 2205/02* (2013.01); *A61M 2210/0618* (2013.01)
(58) Field of Classification Search
CPC .. A61M 16/00; A61M 16/0003; A61M 16/06; A61M 16/0605; A61M 16/0666; A61M 16/0683; A61M 16/0688; A61M 2016/0661; A61M 2205/02; A61M 2205/0238; A61M 2205/58; A61M 2205/583; A61M 2205/584; A61M 2205/60; A61M 2210/0618; A41D 13/1169; A41D 13/1176; A62B 18/084; A62B 23/06
See application file for complete search history.

(56) References Cited

U.S. PATENT DOCUMENTS

| 6,207,875 B1 | 3/2001 | Lindqvist et al. |
| 6,231,548 B1 * | 5/2001 | Bassett ............... A61M 25/02 604/174 |
| 9,327,098 B2 | 5/2016 | Kelvered |
| 2010/0071690 A1 | 3/2010 | Matich |
| 2011/0240038 A1 | 10/2011 | Doshi |

(Continued)

FOREIGN PATENT DOCUMENTS

| CN | 204092334 U | 1/2015 |
| CN | 106381079 A | 2/2017 |

OTHER PUBLICATIONS

International Search Report for PCT/EP2020/076343 dated Sep. 22, 2020.

*Primary Examiner* — Colin W Stuart
(74) *Attorney, Agent, or Firm* — Michael W. Haas (57) ABSTRACT

Securement arrangements for use in securing a patient interface to the skin of a patient include a substrate material having a first surface and an adhesive material disposed on the first surface. The locations of the adhesive material are varied so as to minimize repetitious adherence of the adhesive material to the patient during repeated applications.

10 Claims, 5 Drawing Sheets

(56) References Cited

U.S. PATENT DOCUMENTS

| | | |
|---|---|---|
| 2014/0308338 A1 | 10/2014 | Nierle et al. |
| 2015/0090255 A1 | 4/2015 | Gulliver et al. |
| 2015/0141949 A1 | 5/2015 | Decabooter |
| 2017/0157437 A1* | 6/2017 | Krespi .................. A62B 23/06 |
| 2018/0369530 A1 | 12/2018 | Chodkowski |
| 2019/0076616 A1* | 3/2019 | Walters ............. A61M 16/0497 |
| 2019/0232013 A1 | 8/2019 | Yu et al. |

* cited by examiner

VARIABLE SKIN BREATHABILITY ADHESIVE ARRANGEMENTS FOR PATIENT INTERFACES

CROSS-REFERENCE TO RELATED APPLICATIONS

This patent application claims the priority benefit under 35 U.S.C. § 119(e) of U.S. Provisional Application No. 62/908,027, filed on Sep. 30, 2019, the contents of which are herein incorporated by reference.

BACKGROUND OF THE INVENTION

1. Field of the Invention

The present invention relates to adhesive arrangements, and more particularly to adhesive arrangements for adhering to the skin of a patient. The present invention further relates to adhesive arrangements for use in securing patient interfaces to the skin of a patient.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway, typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion member on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the pressure support device with the airway of the patient, so that a flow of breathing gas can be delivered from the pressure/flow generating device to the airway of the patient.

Traditionally, such patient interface devices have been secured to the face/head of the patient by a headgear component having one or more straps which wrap around all, or a portion, of the patient's head. Recently, adhesive arrangements have been employed, either in-whole, or in-part, to secure patient interface devices to the face of a patient. In such arrangements, many concerns/complaints are related to the strength of the adhesive and the ease of removal of the adhesive. Another major concern/complaint is the formation of red marks on the patient's skin. Red marks are caused by many reasons, one of them including moisture trapped against the skin. Today, adhesives on the market use arrays of holes to allow for breathability of the skin. Many people are familiar with breathable Band-Aid® adhesive bandages that utilize such holes. Adhesive masks on the market are applied to the same portion of skin every single night. In order to have adequate seal the mask is always be applied the same, hence the adhesive element(s) thereof are also applied to the same portion of skin every single night. Because the adhesive mask is applied in the same location every night there can be a breakdown of skin over time due to the adhesive, not to mention increased red marks due to moisture build up.

SUMMARY OF THE INVENTION

Accordingly, as one aspect of the present invention a securement arrangement for use in securing a patient interface to the skin of a patient comprises: a substrate material having a first surface; an adhesive material disposed on the first surface; and a release film disposed on the adhesive material. The release film is sectioned into a plurality of sections and at least one section of the plurality of sections includes a first indicator and a second section of the plurality of sections includes a second indicator different than the first indicator.

The first indicator may comprise at least one of a number or letter, and wherein the second indicator comprises at least one of a number or letter.

The first indicator may comprise a color and the second indicator may comprise another color.

At least a third section of the plurality of sections includes a third indicator different than the first indicator and the second indicator.

The planar substrate material may include a central portion having a plurality of tabs projecting outward therefrom, each of the tabs being structured to wrap up around, and be adhered to the nose of the patient.

As another aspect of the present invention, a kit comprises: a plurality of securement arrangements for use in securing a patient interface to the skin of a patient, each securement arrangement comprising: a substrate material having a first surface and an adhesive material disposed on the first surface. One of the securement arrangements of the plurality is structured to be adhered to a first area or group of areas of the patient and another one of the securement arrangements of the plurality is structured to be adhered to a second area or group of areas that differs from the first area or group of areas.

Each securement arrangement may further comprise a plurality of skin breathability holes, each skin breathability hole extending through the substrate material and the adhesive material, wherein the plurality of skin breathability holes of a first securement arrangement of the plurality of securement arrangements differs from the plurality of skin breathability holes of a second securement arrangement of the plurality of securement arrangements.

The plurality of skin breathability holes of the first securement arrangement may be positioned in a first pattern, and the plurality of skin breathability holes of the second securement arrangement may be positioned in a second pattern different than the first pattern.

The plurality of skin breathability holes of the first securement arrangement may be positioned in a first pattern, the plurality of skin breathability holes of the second securement arrangement may be positioned in a second pattern the same as the first pattern, and the second pattern may be positioned differently relative to the substrate material of the second securement arrangement than the first pattern relative to the substrate material of the first securement arrangement.

The plurality of skin breathability holes of a third securement arrangement of the plurality of securement arrangements may differ from the plurality of skin breathability holes each of the first securement arrangement and the second securement arrangement.

The plurality of skin breathability holes of a third securement arrangement of the plurality of securement arrangements may differ from the plurality of skin breathability holes of each of the first securement arrangement and the second securement arrangement, and the plurality of skin breathability holes of the third securement arrangement may be positioned in a third pattern different than each of the first pattern and the second pattern.

The plurality of skin breathability holes of a third securement arrangement of the plurality of securement arrangements may differ from the plurality of skin breathability holes of each of the first securement arrangement and the second securement arrangement, the plurality of skin breathability holes of the third securement arrangement may be positioned in a third pattern the same as the first pattern and the second pattern, and the third pattern may be positioned differently relative to the substrate material of the third securement arrangement than each of the first pattern relative to the substrate material of the first securement arrangement and the second pattern relative to the substrate material of the second securement arrangement.

The kit may further comprise the patient interface for use in providing a flow of breathing gas to the airway of the patient.

As yet another aspect of the present invention, a method of securing a patient interface to the skin of a patient using a securement arrangement from among a plurality of securement arrangements is provided. Each securement arrangement comprising a substrate material having a first surface and an adhesive material disposed on the first surface. The method comprises: selecting a first securement arrangement of a first design from among the plurality of securement arrangements; securing the patient interface to the patient by adhering the adhesive material of the first securement arrangement to the skin of the patient; detaching the first securement arrangement from the patient; selecting a second securement arrangement of a second design; and securing the second securement arrangement to the patient by adhering the adhesive material of the second securement arrangement to the skin of the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

As required, detailed embodiments of the present invention are disclosed herein; however, it is to be understood that the disclosed example embodiments described herein are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are coupled directly in contact with each other. As used herein, "fixedly coupled" or "fixed" means that two components are coupled so as to move as one while maintaining a constant orientation relative to each other.

As used herein, the statement that two or more parts or components "engage" one another shall mean that the parts exert a force against one another either directly or through one or more intermediate parts or components. As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
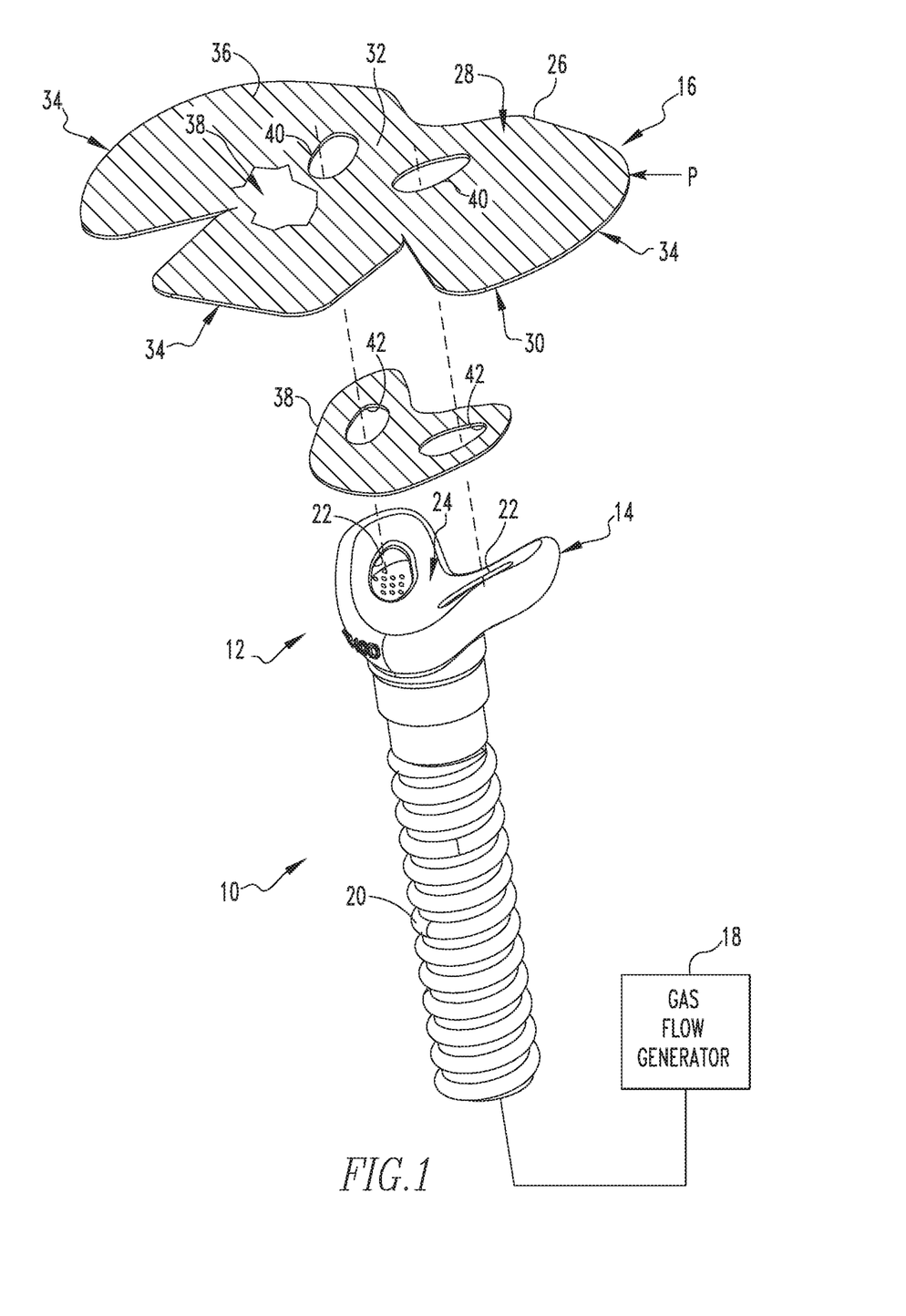
FIG. 1 is a simplified perspective front view of an airway pressure support system including a patient interface and adhesive arrangement which may be aligned utilizing a system in accordance with one non-limiting example embodiment of the present invention.

FIG. 1 is a simplified perspective front view of an airway pressure support system 10 including a patient interface assembly 12 having a patient interface 14 for use in providing a flow of a breathing gas to the airway of a patient (not shown) which may utilize a securement arrangement 16, in accordance with one or more example embodiments of the present invention, for securing patient interface 14 to a patient. Airway pressure support system 10 includes a gas flow generator 18 (shown schematically) and a hose 20 (partially shown schematically) having a first end (not numbered) coupled to gas flow generator 18 and an opposite second end (not numbered) coupled to patient interface 14. Gas flow generator 18 is structured to generate a flow of breathing gas to be delivered to an airway of a patient via hose 20 and patient interface 14.

In the example arrangement shown in FIG. 1, patient interface 14 is in the form of a cradle-like nasal interface for generally engaging the underside of the nose of a patient. Accordingly, patient interface 14 includes a pair nasal apertures 22 defined in a contoured surface 24. In one example embodiment of the present invention, contoured surface 24 and each nasal aperture 22 is custom dimensioned/formed based on facial dimensions of a particular patient. Such custom dimensioning/forming may readily be carried out using 3D scanning and printing techniques known in the art. It is to be appreciated that other arrangements of patient interface 12 may be employed without varying from the scope of the present invention.

Continuing to refer to FIG. 1, securement arrangement 16 is provided for securing patient interface 14 to the face of a patient. Securement arrangement 16 may be mass produced or custom created for the dimensions of a particular patient and is formed from a generally thin (e.g., having a thickness of at least 0.04 mm), substantially planar, substrate material 26 having a first planar surface 28, which faces toward a patient, and a second planar surface 30, opposite first planar surface 28, which faces toward patient interface 14. Planar substrate material 26 may generally be any pliable material such as, for example, without limitation, foam, silicone polyurethane, latex, or any other suitable material. In the example shown in FIG. 1, planar substrate material 26 includes a central portion 32 having a number of tabs 34 projecting outward therefrom, with each of tabs 34 structured to wrap up around, and be secured to the patient's nose. It is to be appreciated that planar substrate material may be of other shapes and/or dimensions without varying from the scope of the present invention.

As discussed in greater detail below, securement arrangement 16 further includes an adhesive material 36 (shown schematically as hatching in FIG. 1, e.g., without limitation, a silicone or acrylic based adhesive layer or any other suitable adhesive layer) provided on first planar surface 28 for use in adhering adhesive arrangement 16 to the skin of a patient. A removable layer of a release film 38 (only a portion of which is shown in FIG. 1) may be provided covering adhesive material 36 for shielding adhesive material 36 until desired to be exposed and adhered to the skin of a patient.

In example system 10 illustrated in FIG. 1, securement arrangement 16 is structured to be positioned generally between patient interface 14 and the skin of the patient. More particularly, securement arrangement 16 is structured to be positioned between contoured surface 24 of patient interface 14 and the skin of the patient and secured to contoured surface 24 via a secondary adhesive arrangement 38 (e.g., a single layer material having upper and lower adhesive surfaces integral therewith or applied thereto) which may be disposed directly on second planar surface 30 of substrate material 26, or alternatively, as a separate element, such as shown in the example of FIG. 1. Additionally, secondary adhesive arrangement 38 may include a foam core for providing dampening resulting from torque due to hose 20. In order to provide for a reliable seal about each nare of the patient, and to allow for the passage of the flow of breathing gas from each of nasal apertures 22 of patient interface 14 to the respective nares of the patient, each of substrate material 26, and similarly secondary adhesive arrangement 38, respectively includes a pair of apertures 40 and 42, respectively, defined therein of similar, and preferably identical shape (e.g., to minimize turbulence, maximize comfort, etc.), as nasal apertures 22.

Embodiments of the present invention vary areas of the patient's skin to which adhesives are placed on successive adhesive applications (e.g., during two or more successive nights for CPAP applications) in order to overcome undesirable shortcomings of conventional adhesive arrangements.

Figure 2A:
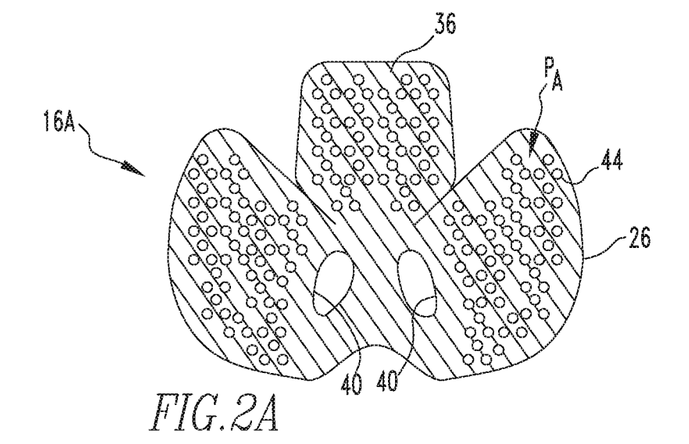
FIGS. 2A-2C are patient facing top views of example securement arrangements utilizing different hole patterns in accordance with example embodiments of the present invention.
Figure 2B:
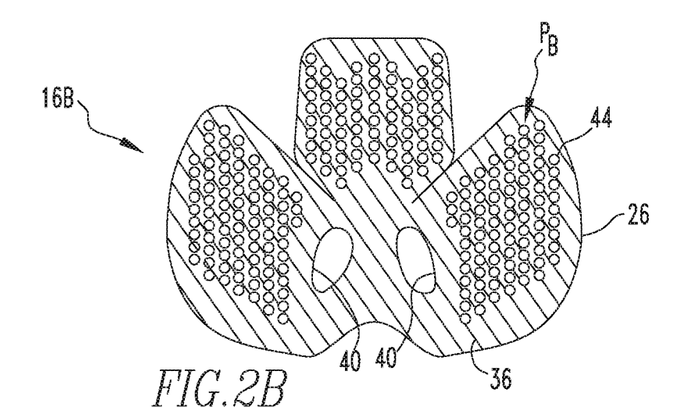
Figure 2C:
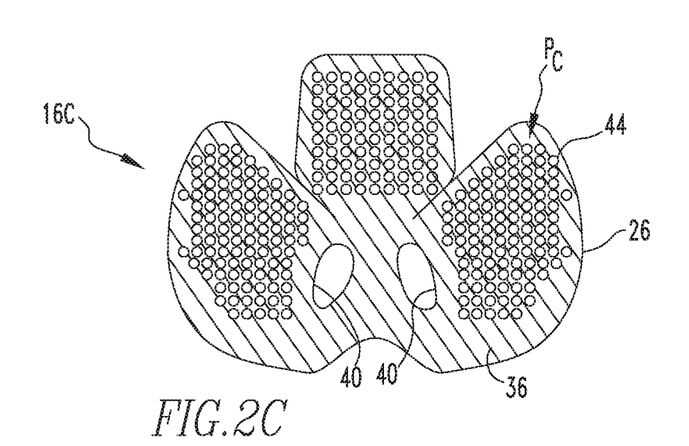

One approach in accordance with the present invention is to change the location of skin breathability holes provided in securement arrangements used on successive occasions, thus varying the areas exposed to ambient air and thus not subjected to adhesive. One example embodiment in accordance with such approach is illustrated in FIGS. 2A-2C which each show a different example securement arrangement 16A, 16B, 16C which may be employed securing patient interface 14 such as described in conjunction with FIG. 1. Like securement arrangement 16 previously discussed, each securement arrangement 16A, 16B, 16C includes substrate material 26 having adhesive material 36 disposed on first planar surface 28 thereof. In the examples shown in FIGS. 2A-2C, each substrate material is of the same outer shape/dimensions. Unlike securement arrangement 16, each securement arrangement 16A, 16B, 16C includes a plurality of skin breathability holes 44 extending through substrate material 26 and adhesive material 36. Skin breathability holes 44 may be formed using a laser, die-cut, or via any suitable technique. Skin breathability holes 44 of each different securement arrangement 16A, 16B, 16C are positioned in a pattern PA, PB, Pc different from the other securements arrangements 16A, 16B, 16C. Accordingly, by using a different one of securement arrangements 16A, 16B, 16C in successive applications, different areas of the skin of a patient are exposed to the breathability holes, and thus the ambient air, instead of adhesive material 36. Although shown as three different securement arrangements 16A, 16B, 16C, it is to be appreciated that such quantity is shown for exemplary purposes only and that two or more different arrangements may be employed without varying from the scope of the present invention.

Figure 3:
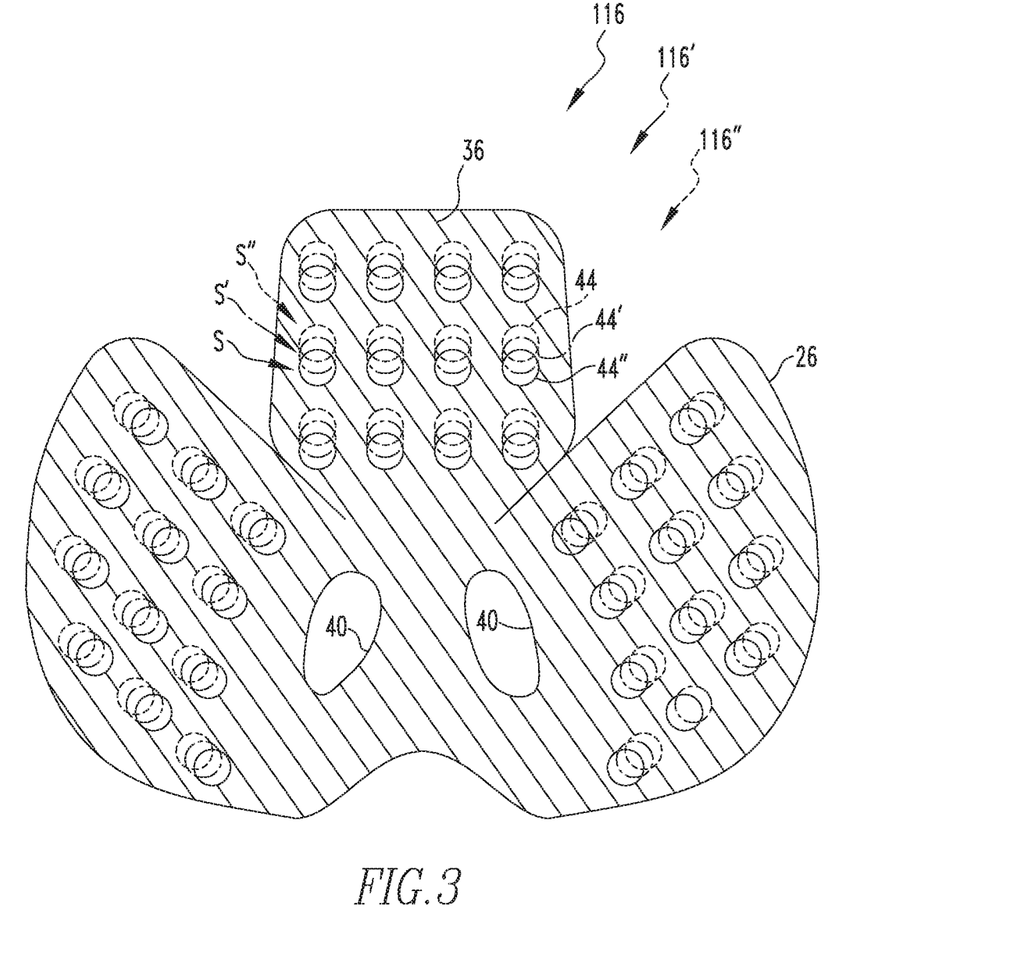
FIG. 3 is a patient facing top view of showing variations of three different example securement arrangements utilizing shifted hole patterns in accordance with an example embodiment of the present invention shown superimposed on each other.

Another approach similar to the one described in conjunction with FIGS. 2A-2C for changing the location of skin breathability holes provided in securement arrangements used on successive occasions is to use the same pattern of skin breathability holes in different securement arrangements but to shift the positioning of such pattern in the different securement arrangements. FIG. 4-3 shows an example of superimposed securement arrangements 116, 116' and 116" in accordance with one example embodiment of the present invention that illustrates such approach. Like securement arrangements 16, 16A, 16B, 16C, previously discussed, securement arrangements 116, 116', 116" include substrate material 26 of the same outer shape/dimension having adhesive material 36 disposed on first planar surface 28 thereof. Also, like securement arrangements 16A, 16B, 16C, securement arrangements 116, 116', 116" include a plurality of skin breathability holes 44, 44', 44" arranged in a predetermined pattern S, S', S". However, unlike securement arrangements 16A, 16B, 16C, second and third variations (116', 116") of securement arrangement 116 includes the same pattern of breathability holes 44 but shifted in position, such as shown schematically by skin breathability holes 44' and 44" shown superimposed in order to illustrate the shifting positioning thereof. Accordingly, by using a different one of securement arrangements 116, 116', 116" in successive applications, different areas of the skin of a patient are exposed to the breathability holes instead of adhesive material 36. Although shown as three different securement arrangements 116, 116', 116", it is to be appreciated that such quantity is shown for exemplary purposes only and that two or more different arrangements may be employed without varying from the scope of the present invention.

Figure 4:
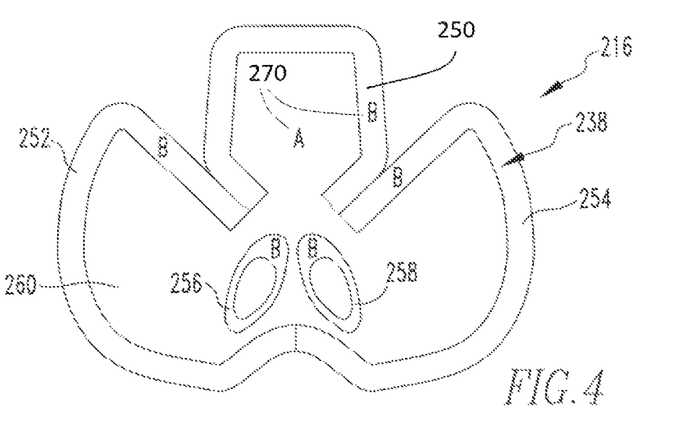
FIGS. 4-6 are patient facing top views of different example securement arrangements utilizing sectioned release film in accordance example embodiments of the present invention.
Figure 5:
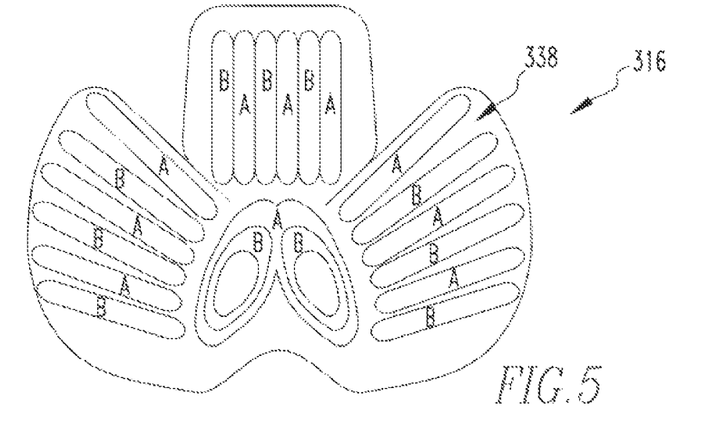
Figure 6:
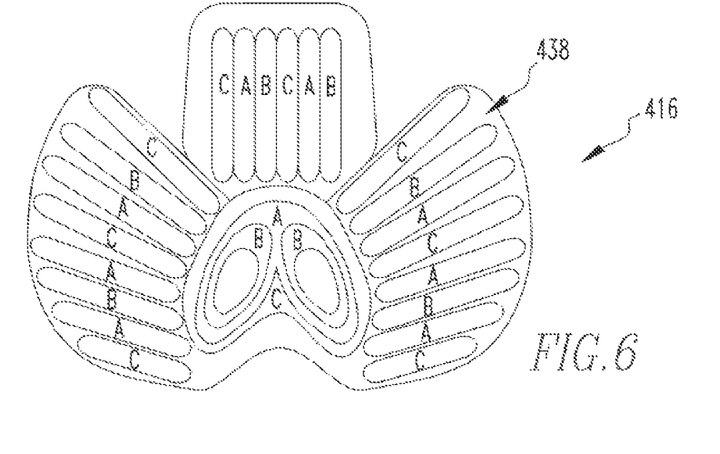
Figure 7A:
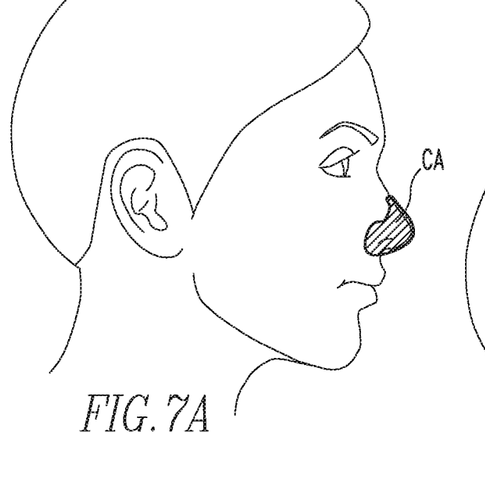
FIGS. 7A-7D are profile views of a patient showing various different adhesive contact areas in accordance with example embodiments of the present invention.
Figure 7B:
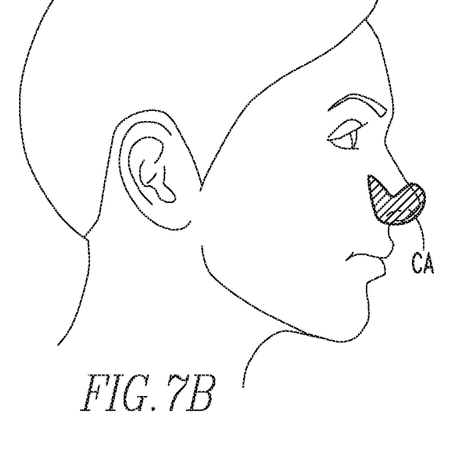
Figures 7C, 7D:
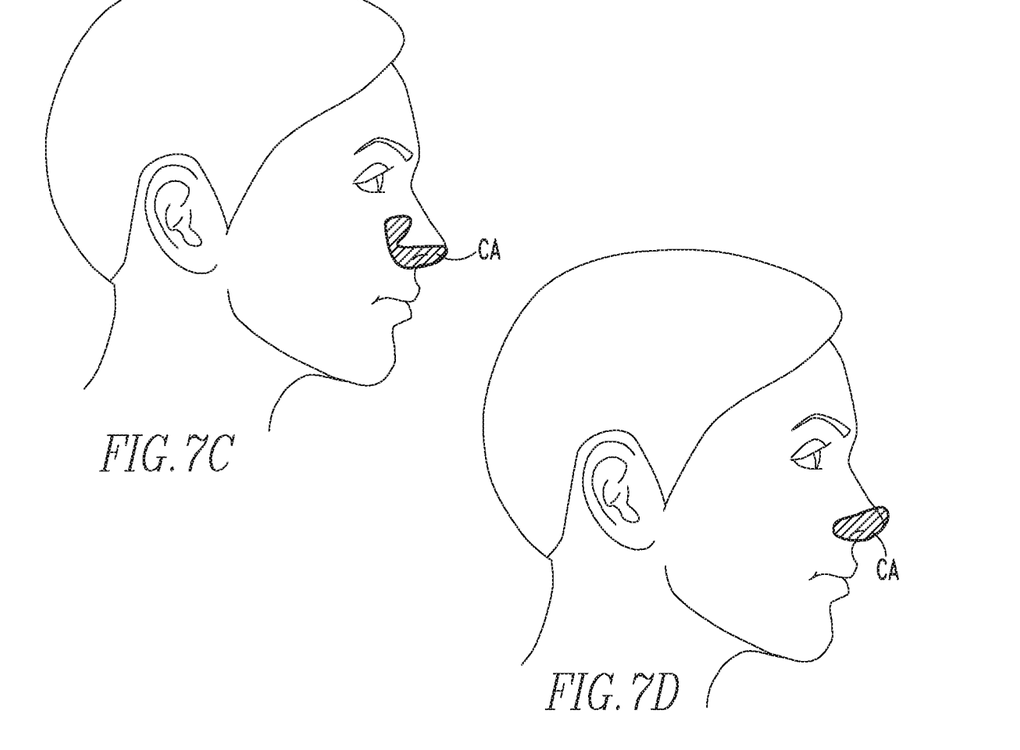

Another approach in accordance with the present invention is to vary the areas to which securement mechanism 16 is adhered to the patient by selectively varying the areas of adhesive material 36 that are actually exposed, and thus used in adhering securement arrangement 16 to the patient at a given time. Such approach is carried out by sectioning release film 38 into different areas or sections, such that for different applications the different areas or sections of release film 38 may be removed while other areas or sections are left in place, thus exposing different areas of adhesive material 36 for adhering to the patient. Some example embodiments of securement arrangements 216, 316, 416 utilizing such approach are shown in FIGS. 4-6. Each of such example embodiments utilize a substrate material, such as substrate material 26 previously described with an overlying adhesive material, such as adhesive material 36 previously discussed, disposed on the substrate material.

Referring to FIG. 4, securement arrangement 216 includes a release film 238 that has been sectioned (e.g., via die cutting or any other suitable arrangement) into multiple sections 250, 252, 254, 256, 258, 260 that may be selectively independently removed from securement arrangement 216, thus exposing an underlying adhesive material (not numbered). In use, either: i.) sections 250, 252, 254, 256 and 258 are removed exposing underlying adhesive material (such as adhesive material 36 previously discussed) for adhering securement arrangement 216 to the patient (with section 260 shielding the patient from the adhesive material thereunder), or ii.) only section 260 is removed exposing the underlying adhesive material for adhering securement arrangement 216 to the patient (with sections 250, 252, 254, 256 and 258 shielding the patient from the adhesive material thereunder). By alternating which section(s) of release film 238 are removed on subsequent applications of embodiments of securement arrangement 216, the same area of the patient's skin is not subjected to adhesive upon consecutive applications. In order to assist a patient or caregiver in removing the correct sections of release film 238, one or more indicators 270 (e.g., without limitation, one or more of numbers, letters, words, colors, graphics, pictures, etc.) may be provided on each section. For example, in the embodiment shown in FIG. 4, letter indicators 270 have been employed, hence section 260 has been labeled with the letter "A", while sections 250, 252, 254, 256 and 258 have been labeled with the letter "B".

FIG. 5 shows a securement arrangement 316 similar to that of FIG. 4 except with the release film 338 thereof sectioned into more, smaller sections.

FIG. 6 shows a securement arrangement 416 similar to that of FIG. 5 except with sections of the release film 438 thereof labeled for three different possible arrangements, i.e., A, B, C of exposed adhesive.

Another approach in accordance with one example embodiment of the present invention is to vary the adhesive contact area by varying the shape of the substrate material used in as the main portion of a securement arrangement or via selective application of the adhesive material (e.g. via printing the adhesive or otherwise selectively placing) to only portions of the substrate material. FIGS. 7A-7D show profile views of a patient showing various different adhesive contact areas CA that may be employed in such arrangements in accordance with example embodiments of the present invention. In applications where adhesive material(s) are selectively placed, one or more of the strength or type of adhesive may also be varied in order to provide a custom application tailored to meet the needs of a particular patient.

From the foregoing, it is thus to be appreciated that the disclosed concept provides for adhesive arrangements that may be alternated so as to reduce skin irritations commonly caused by conventional arrangements. Combinations of such arrangements may be provided in common packaging (e.g., a box or other suitable commercial packaging) as a kit (e.g., without limitation, a week/month supply) for an end user. Although described herein as being used for securing patient interface 14 to a patient, it is to be appreciated that securements arrangements such as described herein as well and the general concepts related thereto may be readily applied to other applications of adhering elements to the skin of a patient without varying from the scope of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A kit comprising:
   a plurality of securement arrangements for use in securing a patient interface to the skin of a patient, each securement arrangement comprising:
   a substrate material having a first surface; and
   an adhesive material disposed on the first surface, wherein one of the securement arrangements of the plurality is structured to be adhered to a first area or group of areas of the patient, and wherein another one of the securement arrangements of the plurality is structured to be adhered to a second area or group of areas that differs from the first area or group of areas
   wherein each securement arrangement further comprises a plurality of skin breathability holes, each skin breathability hole extending through the substrate material and the adhesive material, and wherein the plurality of skin breathability holes of a first securement arrangement in the plurality of securement arrangements differs from the plurality of skin breathability holes of a second arrangement securement in the plurality of securement arrangements.

2. The kit of claim 1, wherein the plurality of skin breathability holes of the first securement arrangement are positioned in a first pattern, and wherein the plurality of skin breathability holes of the second securement arrangement are positioned in a second pattern different than the first pattern.

3. The kit of claim 2, wherein the plurality of skin breathability holes of a third securement arrangement of the plurality of securement arrangements differs from the plurality of skin breathability holes of each of the first securement arrangement and the second securement arrangement, and wherein the plurality of skin breathability holes of the third securement arrangement are positioned in a third pattern different than the first pattern and the second pattern.

4. The kit of claim 1, wherein the plurality of skin breathability holes of the first securement arrangement are positioned in a first pattern, wherein the plurality of skin breathability holes of the second securement arrangement are positioned in a second pattern the same as the first pattern, and wherein the second pattern is positioned differently relative to the substrate material of the second securement arrangement than the first pattern relative to the substrate material of the first securement arrangement.

5. The kit of claim 4, wherein the plurality of skin breathability holes of a third securement arrangement of the plurality of securement arrangements differs from the plurality of skin breathability holes of the first securement arrangement and the second securement arrangement, wherein the plurality of skin breathability holes of the third securement arrangement are positioned in a third pattern the same as the first pattern and the second pattern, and wherein the third pattern is positioned differently relative to the substrate material of the third securement arrangement than the first pattern relative to the substrate material of the first securement arrangement and the second pattern relative to the substrate material of the second securement arrangement.

6. The kit of claim 1, wherein the plurality of skin breathability holes of a third securement arrangement of the plurality of securement arrangements differs from the plurality of skin breathability holes of each of the first securement arrangement and the second securement arrangement.

7. The kit of claim 1, further comprising the patient interface for use in providing a flow of breathing gas to the airway of the patient.

8. A method of securing a patient interface to the skin of a patient using a securement arrangement from among a plurality of securement arrangements, each securement arrangement comprising a substrate material having a first surface and an adhesive material disposed on the first surface, the method comprising:
   selecting a first securement arrangement of a first design from among the plurality of securement arrangements, wherein the first securement arrangement comprises a first plurality of skin breathability holes, each of the first plurality of skin breathability holes extending through the substrate material and the adhesive material;
   securing the patient interface to the patient by adhering the adhesive material of the first securement arrangement to the skin of the patient;
   detaching the first securement arrangement from the patient;
   selecting a second securement arrangement of a second design, wherein the second securement arrangement comprises a second plurality of skin breathability holes, each of the second plurality of holes skin breathability hole extending through the substrate material and the adhesive material, and wherein the first plurality of skin breathability holes differs from the second plurality of skin breathability holes; and
   securing the second securement arrangement to the patient by adhering the adhesive material of the second securement arrangement to the skin of the patient.

9. The method of claim 8, wherein the plurality of skin breathability holes of the first securement arrangement are positioned in a first pattern, and wherein the plurality of skin breathability holes of the second securement arrangement are positioned in a second pattern different than the first pattern.

10. The method of claim 8, wherein the plurality of skin breathability holes of the first securement arrangement are positioned in a first pattern, wherein the plurality of skin breathability holes of the second securement arrangement are positioned in a second pattern the same as the first pattern, and wherein the second pattern is positioned differently relative to the substrate material of the second securement arrangement than the first pattern relative to the substrate material of the first securement arrangement.

\* \* \* \* \*